United States Patent
Maeda et al.

[11] Patent Number: 6,056,866
[45] Date of Patent: May 2, 2000

[54] STERILIZING APPARATUS AND METHOD FOR MEDICAL INSTRUMENTS

[75] Inventors: Toyoyuki Maeda, Kawachinagano; Seiji Terakura, Ikoma; Kouzaburo Hayashi, Osaka, all of Japan

[73] Assignee: Kaigen Co., Ltd., Osaka, Japan

[21] Appl. No.: 09/407,072

[22] Filed: Sep. 28, 1999

Related U.S. Application Data

[63] Continuation of application No. 08/698,425, Aug. 15, 1996.

[30]  Foreign Application Priority Data

Aug. 17, 1995  [JP]  Japan .................................. 7-209543
Jul. 24, 1996  [JP]  Japan .................................. 8-194488

[51] Int. Cl.⁷ .................................................. C02F 1/461
[52] U.S. Cl. .......................... 205/464; 205/746; 205/747; 205/751; 204/263
[58] Field of Search ..................................... 205/464, 746, 205/747, 751; 204/263

[56]  References Cited

U.S. PATENT DOCUMENTS

| | | |
|---|---|---|
| 4,867,856 | 9/1989 | Okazaki .................. 204/263 |
| 5,316,646 | 5/1994 | Arai . | |
| 5,543,030 | 8/1996 | Shiramizu et al. . |
| 5,578,193 | 11/1996 | Aoki et al. . |

FOREIGN PATENT DOCUMENTS

| | | |
|---|---|---|
| 3430631 | 2/1986 | Germany . |
| 2085488 | 1/1995 | Japan . |
| 737114 | 7/1995 | Japan . |

OTHER PUBLICATIONS

Translation of Japanese Official Action dated Jun. 1, 1999.
Translation of JP Laid Open Utility Model Application No. 7-37114 cited reference in Japanese Official Action dated Jun. 1, 1999.

*Primary Examiner*—Arun S. Phasge

[57] ABSTRACT

The present invention provides a sterilizing apparatus and a sterilizing method for medical instruments enabling easy sterilization of medical instruments in a short time.

There are provided an electrolyzation device which produces acidic electrolytic water as a sterilization liquid by electrolyzing electrolytic water stored in an electrolytic cell, a sterilization bath for storing medical instruments to be sterilized by the acidic electrolytic water, and a circulation device which circulates the acidic electrolytic water between the electrolytic cell and sterilization bath thereby to sterilize the medical instruments.

16 Claims, 9 Drawing Sheets

STERILIZING APPARATUS AND METHOD FOR MEDICAL INSTRUMENTS

This application is a continuation of co-pending Application No. 08/698,425, filed on Aug. 15, 1996, still pending, the entire contents of which are hereby incorporated by reference.

BACKGROUND OF THE INVENTION

The present invention relates to a sterilizing apparatus and a sterilizing method for automatically sterilizing medical instruments such as endoscopes or the like using oxidation water.

The use of endoscopes has rapidly spread in recent years to inspect upper and lower alimentary canal such as the esophagus, stomach, etc. and the large intestine, etc., inviting an increase in the number of the endoscopic inspections carried out in each facility. In spite of this fact, however, every facility owns only a few endoscopes due to their high unit cost. Although the endoscopes are cleaned and sterilized at the end of a day's use before being kept in the depositary, the sterilization of the endoscopes cannot be deemed sufficient, because the frequency of use is increased, although the facility possesses only a small number of endoscopes. In other words, the frequency of use of each endoscope is increased, or due to time and labor problems. The endoscopes shared among patients are consequently not clean, resulting in a fear that germs and virus adhering to the endoscopes are spread among the patients. Infection by the germs and virus has drawn particular attention lately in accordance with the increased use of the endoscopes.

Any sterilizers for the endoscopes in the market use a sterilizing liquid or a disinfectant including a liquid medicine, e.g., a glutaraldehyde formulation solution, which require not only soaking the endoscopes in the sterilizing liquid, but also rinsing the sterilization liquid, (ie, several tens of minutes in total). The endoscopes shared among the patients cannot be sterilized in a simple manner and in a short time by the above conventional sterilizers.

SUMMARY OF THE INVENTION

Accordingly, an object of the present invention is to provide a sterilizing apparatus and a sterilizing method enabling easy sterilization of medical instruments in a short time.

In accomplishing these objects, according to one aspect of the present invention, a sterilizing apparatus for medical instruments is provided comprising:

an electrolyzation device which has an electrolytic cell and produces acidic electrolytic water for use as a disinfectant by electrolyzing electrolytic water stored in the electrolytic cell;

a sterilization bath for storing medical instruments to be sterilized by the acidic electrolytic water; and a circulation device which circulates the acidic electrolytic water between the electrolytic cell and sterilization bath thereby to sterilize the medical instruments.

According to another aspect of the present invention, there is provided a sterilizing apparatus for medical instruments which is so constituted as to produce an ante-sterilization acidic electrolytic water for use as a disinfectant by electrolyzing an electrolytic water, sterilize medical instruments using the produced ante-sterilization acidic electrolytic water, electrolyze the post-sterilization acidic electrolytic water after sterilizing fresh medical instruments, thereby to produce the ante-sterilization acidic electrolytic water again, and circulate acidic electrolytic water, thereby sterilizing the medical instruments.

By the above construction of the present invention, the electrolyzation device produces the acidic electrolytic water in the electrolytic cell for sterilizing the medical instruments set in the sterilization bath. On the other hand, the circulation device supplies the acidic electrolytic water produced in the electrolytic cell to the sterilization bath, and also returns the acidic electrolytic water from the sterilization bath to the electrolytic cell, thus circulating the acidic electrolytic water between the electrolytic cell and sterilization bath thereby to sterilize medical instruments. When acidic electrolytic water is used as a disinfectant as discussed above, since the acidic electrolytic water remaining on the surface of the sterilized medical instruments is changed to neutral water over time, the sterilizing apparatus of the present invention eliminates the necessity for rinsing away the disinfectant after the sterilization, thereby achieving sterilization in a short time. Moreover, the sterilizing apparatus facilitates sterilization of medical instruments, because it is enough to simply put the medical instruments in the sterilization bath. When the acidic electrolytic water is circulated to sterilize endoscopes, it is effective in that the consumption of water is decreased, the exchange of water is not required, and water feed/discharge piping to the sterilizing apparatus is eliminated.

According to another aspect of the present invention, a sterilizing method for medical instruments is provided which comprises:

a producing step for producing acidic electrolytic water for use as a disinfectant by electrolyzing electrolytic water stored in an electrolytic cell;

a setting step for setting medical instruments to be sterilized by the acidic electrolytic water in a sterilization bath; and a circulating/sterilizing step for circulating the acidic electrolytic water between the electrolytic cell and sterilization bath to thereby to sterilize the medical instruments.

BRIEF DESCRIPTION OF THE DRAWINGS

These and other aspects and features of the present invention will become clear from the following description, taken in conjunction with the preferred embodiments thereof with reference to the accompanying drawings, in which.

DETAILED DESCRIPTION OF THE PREFERRED EMBODIMENTS

Before the description of the present invention proceeds, it is to be noted that like parts are designated by like reference numerals throughout the accompanying drawings.

A sterilizing apparatus for medical instruments in one mode of the present invention will be described below with reference to the drawings. A sterilizing method for medical instruments in one mode of the present invention is executed by this sterilizing apparatus. It is to be noted here that a filter 60 corresponds to a removing member described in claims in one form with the same function, and a nozzle 502 corresponds to a gas feeder in claims in one form with the same function.

Figure 1:
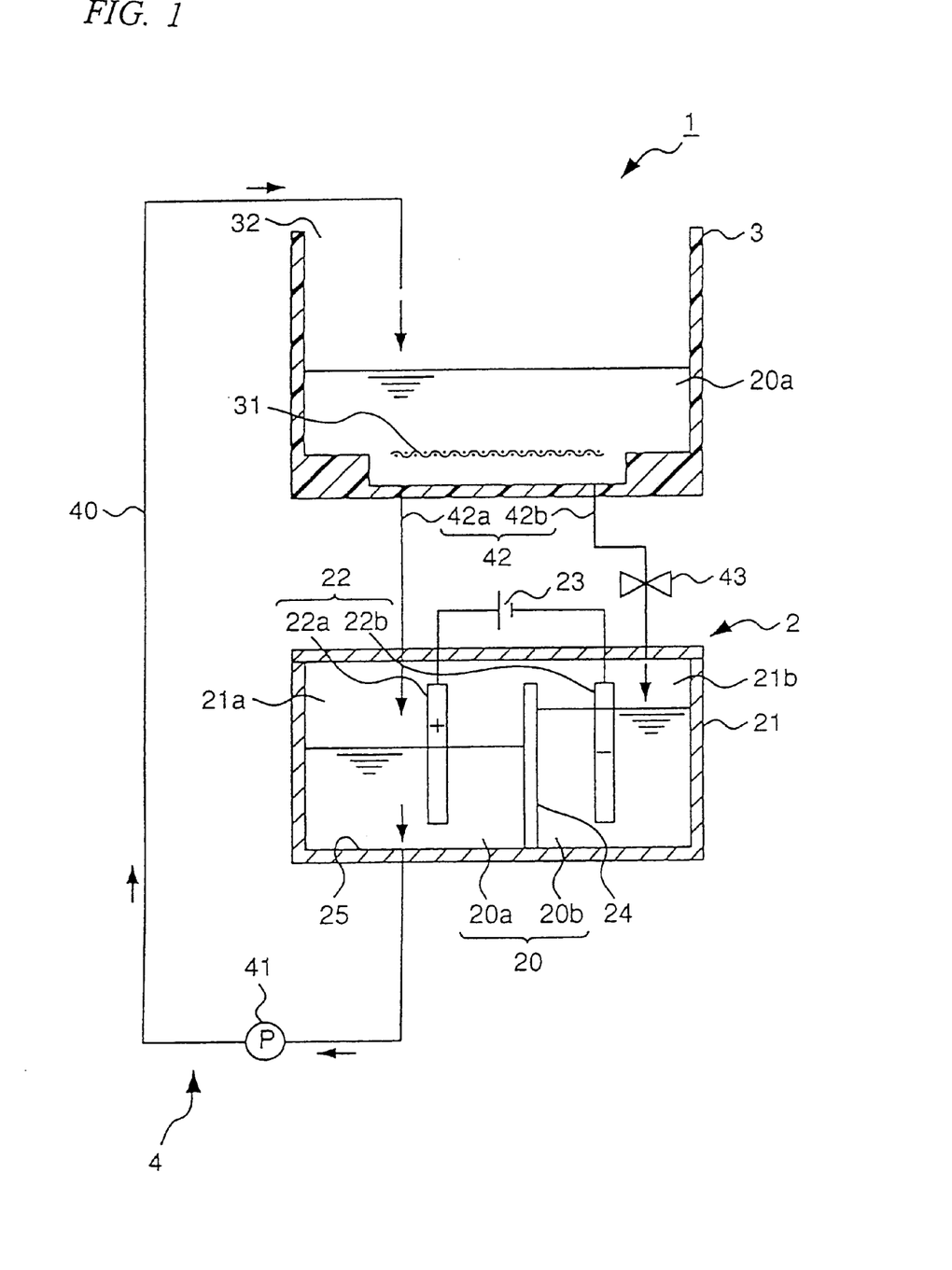
FIG. 1 is a schematic view showing an example of the constitution of a sterilizing apparatus for medical instruments in one embodiment of the present invention.

FIG. 1 shows the basic schematic structure of a sterilizing apparatus 1 for medical instruments according to an embodiment to be discussed below. Generally, the sterilizing apparatus 1 has an electrolyzation device 2, a sterilization bath 3 and a circulation device 4.

The electrolyzation device 2 has an electrolytic cell 21 storing electrolytic water 20, a positive electrode 22*a* and a negative electrode 22*b* (generally referred to as electrodes 22) immersed in the electrolytic water 20 to produce acidic electrolytic water 20*a* and alkalic electrolytic water 20*b* through the electrolyzation of the electrolytic water 20, a power source 23 for supplying direct current to electrodes 22, an ion exchange film 24 set in the electrolytic cell 21 to form a wall as a boundary between the acidic electrolytic water 20*a* and the alkalic electrolytic water 20*b*. The amount of the electrolytic water 20 stored in the electrolytic cell 21 is, for example approximately 10 l so that the acidic electrolytic water can be generated in a short time. To facilitate electrolyzation, the electrolytic water 20 is a 0.05% aqueous solution of sodium chloride obtained by dissolving 5 g of sodium chloride in 10 l of plain water. The ion exchange film 24 maintains a capacity ratio of acidic electrolytic water cell 21*a* and alkalic electrolytic water cell 21*b* to be for example 6:4. The reason why the capacity of the cell 21*a* is made larger than that of the cell 21*b* is to use the acidic electrolytic water 20*a* to sterilize medical instruments in the sterilizing apparatus 1. The electrodes 22 are obtained by plating a titanium plate with platinum. As indicated in the drawing, the positive electrode 22*a* is spaced approximately 95 mm from the negative electrode 22*b* via the ion exchange film 24 to be opposed generally in parallel to each other. The power source 23 feeds a starting current of 5 A of less for the electrolyzation to the electrode 22 until the electrolytic water 20 reaches a target specific value (to be described later) and feeds a keep current of about 1 A after the target specific value is achieved to maintain the target specific value. The starting current is not larger than 5 A, as above, in order to prevent the electrolytic water 20 from being suddenly electrolyzed to thereby restrict the generation of free chlorine as much as possible. The concentration of generated residual chlorine is about 6 ppm. The ion exchange film made 24 is a cation exchange film of a fluorocarbon resin, for example.

The sterilization bath 3 is, for example, U-shaped in cross section as shown in FIG. 1 and formed of a resin material such as vinyl chloride or the like. Within the sterilization bath 3 is disposed, for instance, a wire screen 31 on which medical instruments such as syringes, needles, endoscope main bodies, endoscope accessories, etc. are placed.

Figure 3:
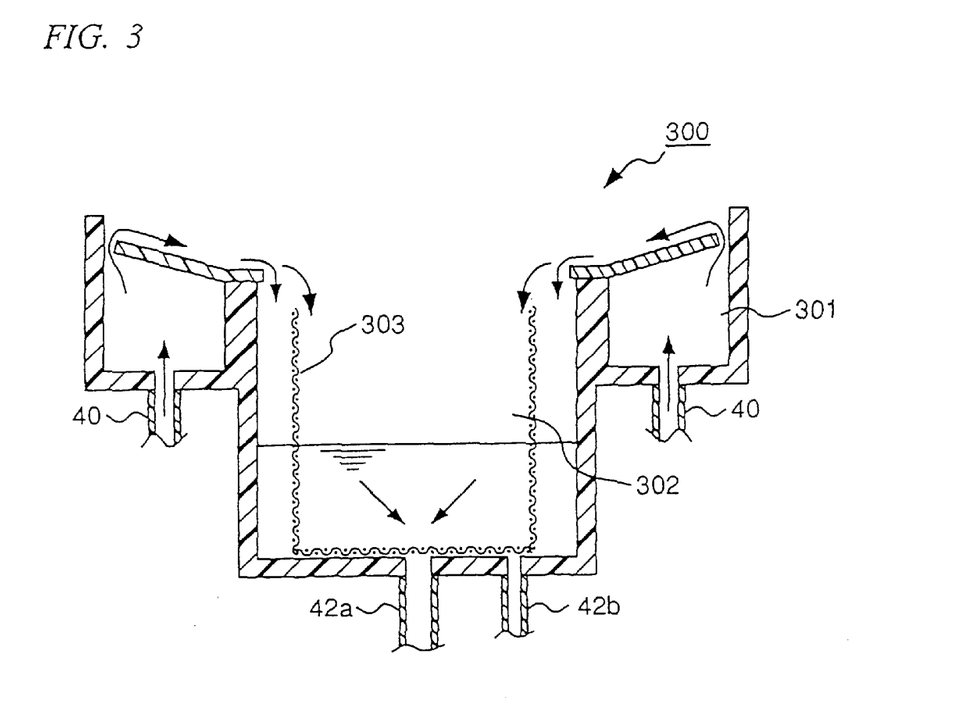
FIG. 3 is a sectional view of a modified sterilization bath in the sterilizing apparatus shown in FIGS. 1 and 2.

The sterilization bath 3 may be formed differently, for example, as indicated in FIG. 3. The same components as in FIG. 1 are designated by the same reference numerals in FIG. 3 and the specific description therefor will be omitted. The sterilization bath 300 has a first sterilization part 301 and a second sterilization part 302. The acidic electrolytic water 20*a* is supplied to the first sterilization part 301 to sterilize endoscopes, while medical instruments are sterilized in the second sterilization part 302 by the acidic electrolytic water 20*a* overflowing from the first sterilization part 301. The overflow method is employed so as to completely immerse the endoscopes in the acidic electrolytic water. A basket 303 of metal meshwork is set in the second sterilization part 302 to accommodate medical instruments therein.

The circulation device 4 is provided with a feed piping 40 preferably formed of silicon rubber, a pump 41 for feeding the acidic electrolytic water 20*a* in the electrolytic cell 21 into the sterilization bath 3 through the feed piping 40 and, a return piping 42 preferably formed of silicon rubber to return the acidic electrolytic water 20*a* supplied to the sterilization bath 3 to the electrolytic cell 21. The above feed piping 40 has one end opened at a bottom part 25 of the acidic electrolytic water cell 21*a* of the electrolytic cell 21 and the other end opened to the sterilization bath 3. The return piping 42 has a return piping 42*a* for guiding the acidic electrolytic water 20*a* in the sterilization bath 3 to the acidic electrolytic water cell 21*a* of the electrolytic cell 21 and a return piping 42*b* for guiding the acidic electrolytic water 20*a* to the alkalic electrolytic water cell 21*b* via a valve 43. As will be described later, the valve 43 is opened when the 0.05% sodium chloride solution is injected to the sterilization bath 3 when the sterilizing apparatus is started, whereby 60% of the 0.05% sodium chloride solution is fed to the acidic electrolytic water cell 21*a*, with the remaining 40% fed to the alkalic electrolytic water cell 21*b*. After the sterilization operation is started, the valve 43 is closed to prevent the acidic electrolytic water 20*a* in the sterilization bath 3 from returning to the alkalic electrolytic water cell 21*b*. The acidic electrolytic water 20*a* in the sterilization bath 3 drops because gravity causes it to drain to the acidic electrolytic water cell 21*a* through the return piping 42*a*.

Figure 2:
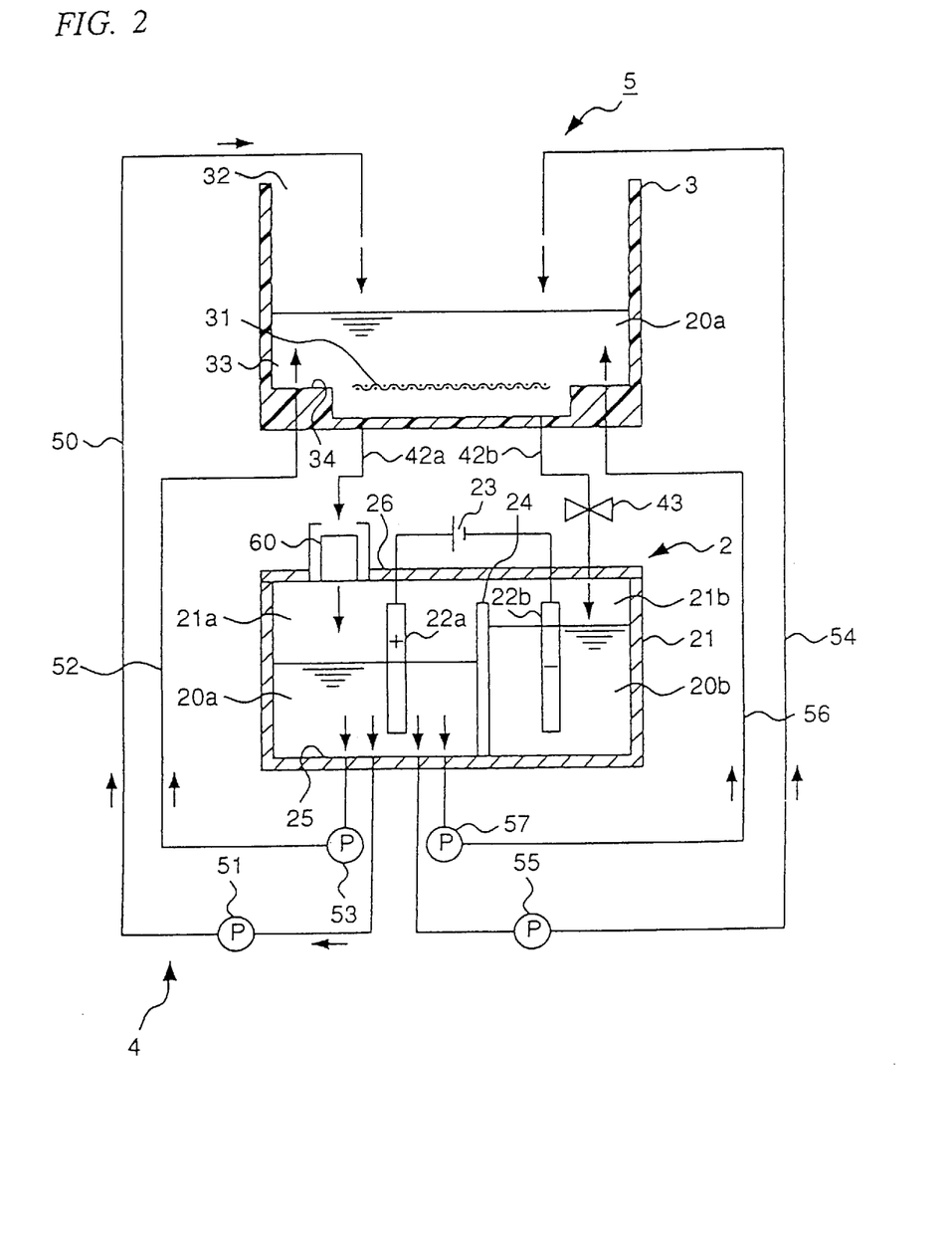
FIG. 2 is a schematic view showing an example of the constitution of a sterilizing apparatus for medical instruments in a different embodiment of the present invention.

FIG. 2 shows a sterilizing apparatus 5 for medical instruments in a different embodiment. The same parts as those of FIG. 1 are designated by the same reference numerals in FIG. 2, the description of which will be omitted.

The above-described sterilizing apparatus 1 is so constituted as to supply the acidic electrolytic water 20*a* into the sterilization bath 3 only from an upper part 32 of the sterilization bath 3 as shown in FIG. 1. On the other hand, in the sterilizing apparatus 5, in FIG. 3 in order to increase sterilization efficiency for the medical instruments set in the sterilization bath 3, a second system comprising a feed piping 52 and a pump 53 to supply acidic electrolytic water 20*a* into the sterilization bath 3 from a bottom part 33 of the sterilization bath 3 is also provided, in addition to a first system of feed piping 50 and pump 51 which is the same system as that of the sterilizing apparatus 1. Moreover, another set of a piping and a pump is arranged for each of the first and second systems. That is, four feed pipings 50, 52, 54, 56 of two systems are installed in the circulation device 4 of the sterilizing apparatus 5.

Figure 5:
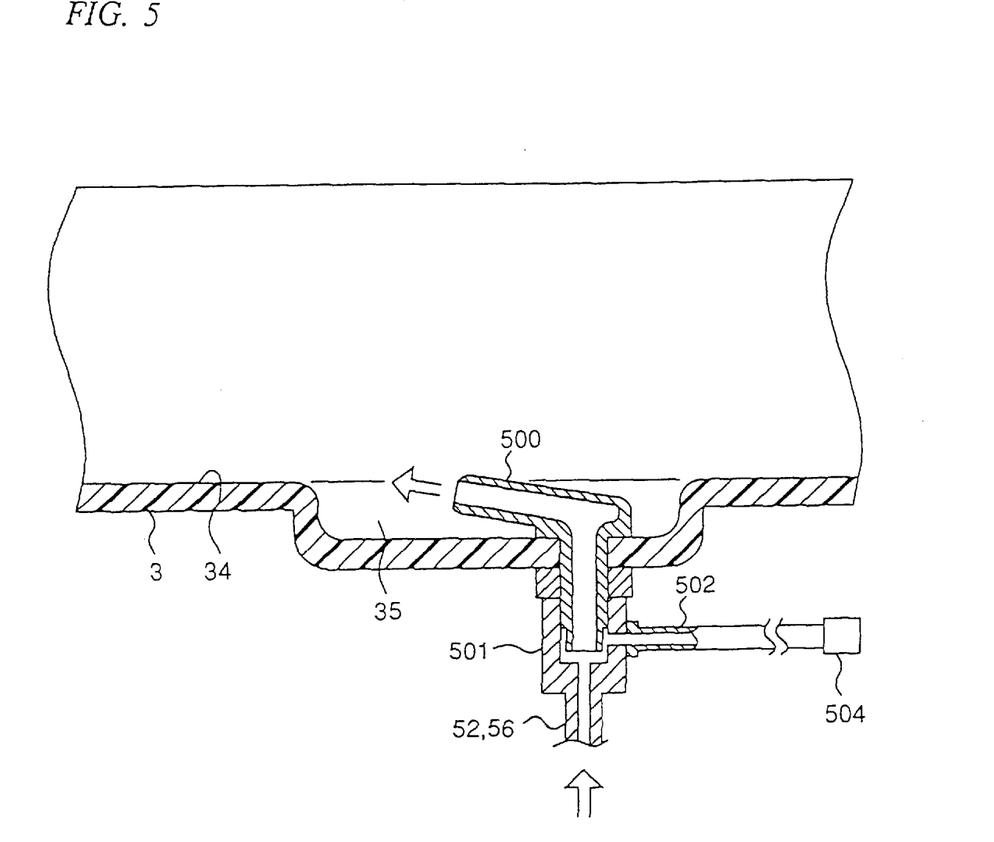
FIG. 5 is a sectional view of a connection end part connected to the sterilization bath in FIG. 2 or 3 and a nozzle.

In a more preferred embodiment, a connection end part 500 (see FIG. 5) where each feed piping 52, 56 feeding the acidic electrolytic water 20*a* into the sterilization bath 3 at the bottom part 33 of the sterilization bath 3 is connected and opened to the bottom part 33 is formed inside the sterilization bath 3 and so oriented as to generate a flow of the acidic electrolytic water 20a in the sterilization bath 3. The flow of the acidic electrolytic water brought about in the sterilization bath 3 improves the sterilization efficiency for medical instruments set in the sterilization bath 3. In order to generate the above flow of the acidic electrolytic water, the connection end part 500 is arranged at the bottom part 33 of the sterilization bath 3 in a manner to jet the acidic electrolytic water 20a out, for instance, in parallel to a bottom face 34 of the sterilization bath 3. It is more favorable if the connection end part 500 is arranged to be nearly completely accommodated in a recessed part 35 formed at the bottom face 34 of the sterilization bath 3 at an acute angle between the direction in which the acidic electrolytic water 20a is jetted and the bottom face 34, as indicated in FIG. 5. The recessed part 35 is provided to cause the connection and part 500 to project less from the bottom face 34 thereby to refrain the connection end part 500 from being an obstacle to the medical instruments set in the sterilization bath 3.

If a nozzle 502 is set at a part 501 where the feed piping 52, 56 is connected to the sterilization bath 3, is also desirable to suck air into the feed piping 52, 56 by the flow of the acidic electrolytic water 20a in the feed piping 52, 56, as shown in FIG. 5. While the nozzle 502 feeds the air to the interior of the feed piping 52, 56 as mentioned above, an opening part at one end of the nozzle 502 is positioned higher than the water level in the sterilization bath 3 so as to prevent the acidic electrolytic water 20a from leaking outside the piping via the nozzle 502. Alternatively, the nozzle 502 may be connected to an air pump 504 thereby to forcibly feed the air into the piping 52, 56. The set position for the nozzle 502 is desirably the above part 501, but it is not limited to this position and may be in an adequate position between the pump 53, 57 and the sterilization bath 3. The nozzle 502 may also be arranged at a suitable position between the pump 51, 55 of the feed piping 50, 54 and the sterilization bath 3.

Figure 4:
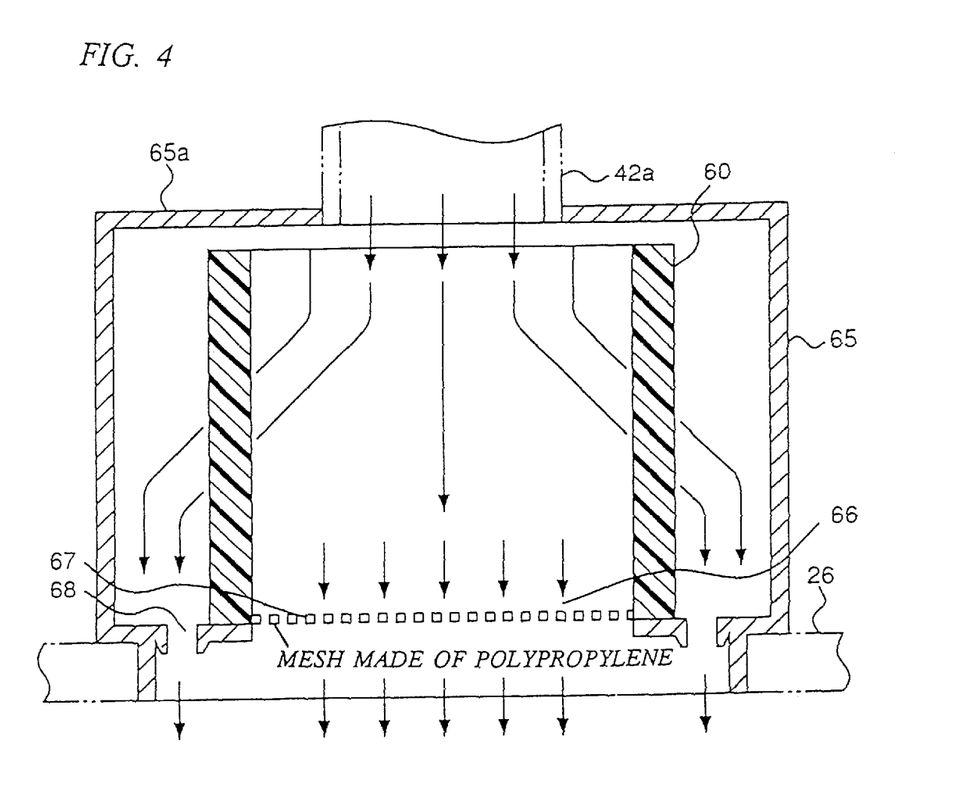
FIG. 4 is a sectional view showing the constitution of a filter part shown in FIG. 2.

A filter 60 for removing solid substance in the acidic electrolytic water 20a discharged from the sterilization bath 3 is disposed in the circulation device 4 in the sterilizing apparatus 5, more specifically, at the return piping 42a which returns the acidic electrolytic water 20a in the sterilization bath 3 to the acidic electrolytic water cell 21a of the electrolytic cell 21 (see FIG. 4). A case 65 accommodating the filter 60 is placed on a top plate 26 of the electrolytic cell 21. The acidic electrolytic water 20a passing the filter 60 thus falls into the acidic electrolytic water cell 21a.

The filter 60 is described with reference to FIG. 4. The filter 60 is made of polypropylene in a cylindrical form, as illustrated, to trap solid material of a size of not smaller than several tens of $\mu$m or so. The filter 60 is fitted inside the case 65. The return piping 42a is connected at a predetermined position of an upper plate 65a of the case 65 to feed the acidic electrolytic water 20a from the sterilization bath 3 to the side of the inner periphery of the cylindrical filter 60. A net-like coarse filter 67 of polypropylene is provided at a bottom part 66 of the case 65 so as to filter the acidic electrolytic water 20a dropping to the acidic electrolytic water cell 21a directly through a cylinder or trunk part of the filter 60, without passing through the filter 60. Further, an opening 68 is formed to drop the acidic electrolytic water 20a passing the filter 60 to the acidic electrolytic water cell 21a. The case 65 is so designed as to allow the filter 60 to be easily positioned/detached to the case 65.

Figure 6:
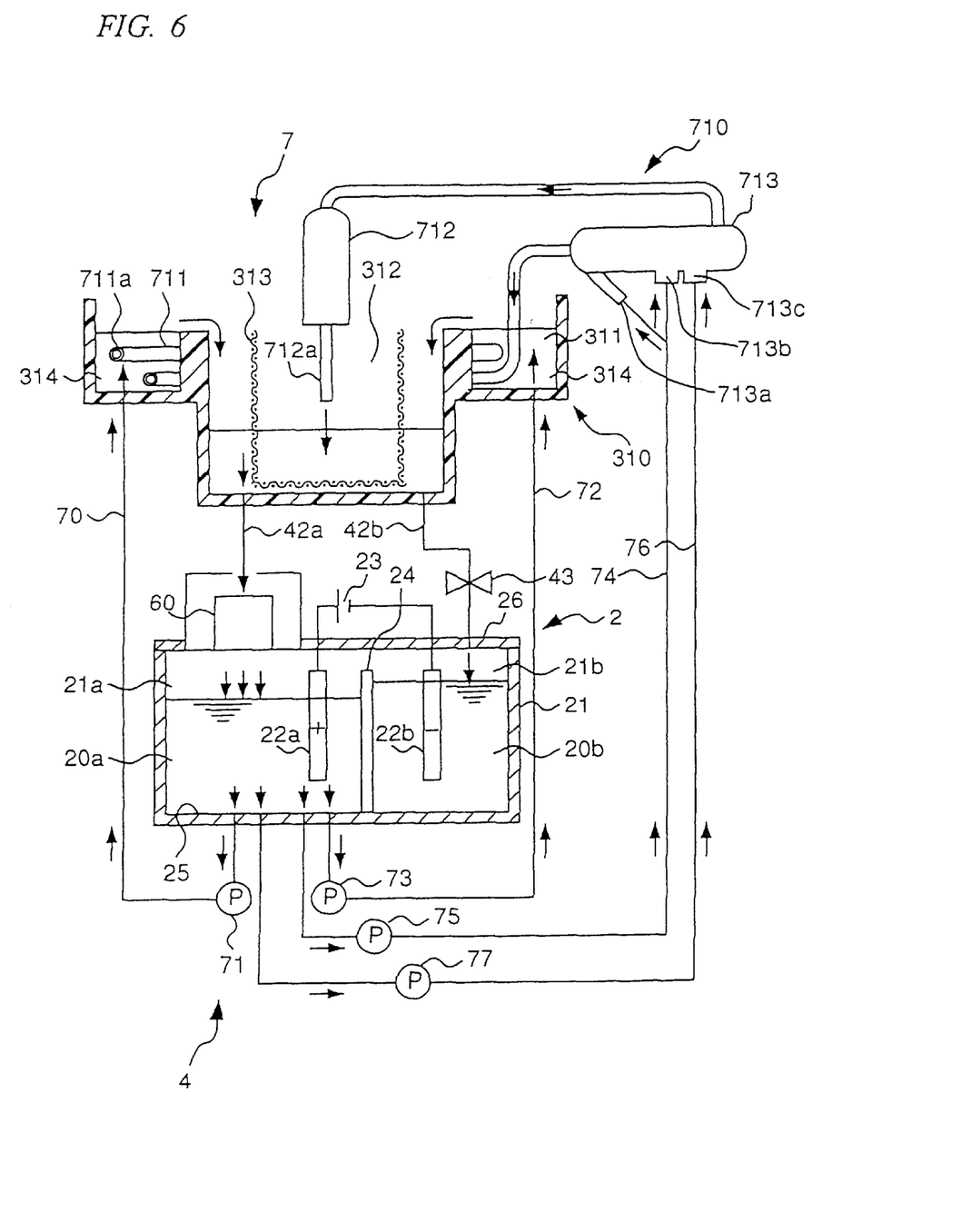
FIG. 6 is a schematic view showing an example of the constitution of a sterilizing apparatus for medical instruments in a further different embodiment of the present invention, which is particularly fit for the sterilization of endoscopes.

FIG. 6 indicates a sterilizing apparatus 7 for medical instruments in a further different embodiment. Among the parts shown in FIG. 6, those which are the same as in FIG. 2 are represented by the same reference numerals and the description therefor will be omitted here. The sterilizing apparatus 7 is particularly targeted to sterilizing endoscopes. Moreover, the sterilizing apparatus 7, with the aim of preventing the infection among patients and sterilizing the endoscopes in a short time, sterilizes only an operative part of the endoscopes having germs, etc. adhered thereto as a result of the inspection to patients. Therefore, although a manipulation part 713 of the endoscope and the periphery thereof are generally not sterilized, it is possible to sterilize the manipulation part 713 as well in a sterilization bath of the apparatus to be described later.

In the sterilizing apparatus 7, the circulation device 4 includes feed pipings 70, 72, 74, 76 and pumps 71, 73, 75, 77. The feed pipings 70, 72 and pumps 71, 73 feed the acidic electrolytic water 20a to a sterilization bath 310 from two points at a bottom part 314 of the sterilization bath 310. The feed piping 74 and pump 75 feed the acidic electrolytic water 20a mainly through a forceps opening 713a and a suction button opening 713b of the manipulation part 713 of an endoscope 710 into an internal insertion part 711 to be inserted into the body of a patient. Meanwhile, the feed piping 76 and pump 77 feed the acidic electrolytic water 20a mainly through an air/water feed button opening 713c of the manipulation part 713 into a connection part 712 to be connected to a light source device for the endoscope (not shown).

The sterilization bath 310 of the sterilizing apparatus 7 includes an annular sterilization bath 311 where the internal insertion part 711 of the endoscope 710 is stored and an accessory sterilization bath 312 integrally formed with the sterilization bath 311 which is located at a central part of the sterilization bath 311 and to which the acidic electrolytic water 20a overflowing from the sterilization bath 311 runs in. The insertion part 711, wound along the outline of the sterilization bath 311, is accommodated in the sterilization bath 311. Accessories of the endoscope 710 and other medical instruments are kept in a metal netting 313 in the sterilization bath 312. The sterilization bath 312 holds one end of the connection part 712.

In the sterilizing apparatus 7 of the above-described constitution, the outer face of the insertion part 711 of the endoscope 710 is sterilized by the acidic electrolytic water 20a filled in the sterilization bath 311, and moreover, the interior of each of the manipulation part 713 including the forceps opening 713a, insertion part 711 and connection part 712 is sterilized by the acidic electrolytic water 20a fed to the endoscope 710 through the feed pipings 74, 76. The acidic electrolytic water 20a supplied into the insertion part 711 is discharged out from a front end 711a of the insertion part 711 to the sterilization bath 311. On the other hand, the acidic electrolytic water 20a supplied into the connection part 712 is discharged from a connection end part 712a of the connection part 712 to the accessory sterilization bath 312.

Figure 7:
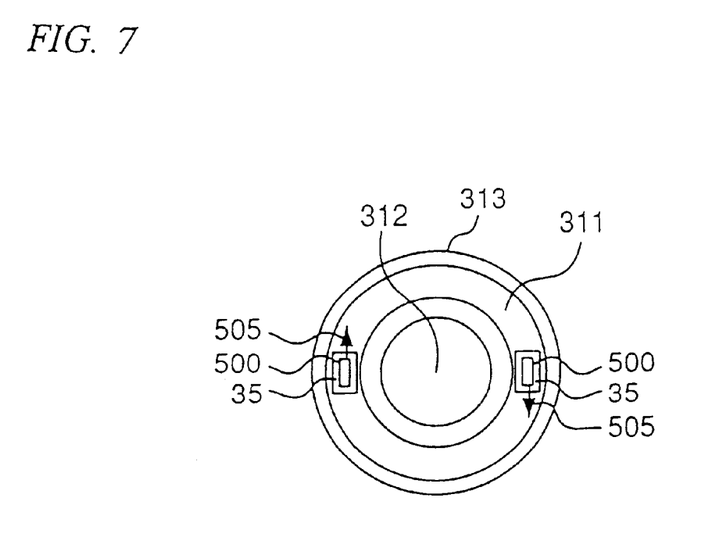
FIG. 7 is a plan view of the sterilization bath shown in FIG. 6 and explaining the position where the connection end parts are formed.

The sterilizing apparatus 7 has the recessed part 35 as described in the preceding embodiments at the bottom part 314 of the sterilization bath 310. The connection end part 500 is formed to be nearly totally accommodated in the recessed part 35. Also the nozzle 502 is provided. The connection end part 500 is oriented to jet the acidic electrolytic water 20a in a direction indicated by an arrow 505 in FIG. 7 so as to form a flow of the water in one direction along the outline of the sterilization bath 311. Moreover, the connection end parts 500 are separated 180° on the circumference of the sterilization bath 311 as in FIG. 7. In the meantime, the insertion part 711 is wound in an opposite direction to the direction of the water flow and accommodated in the sterilization bath 311.

Figure 8:
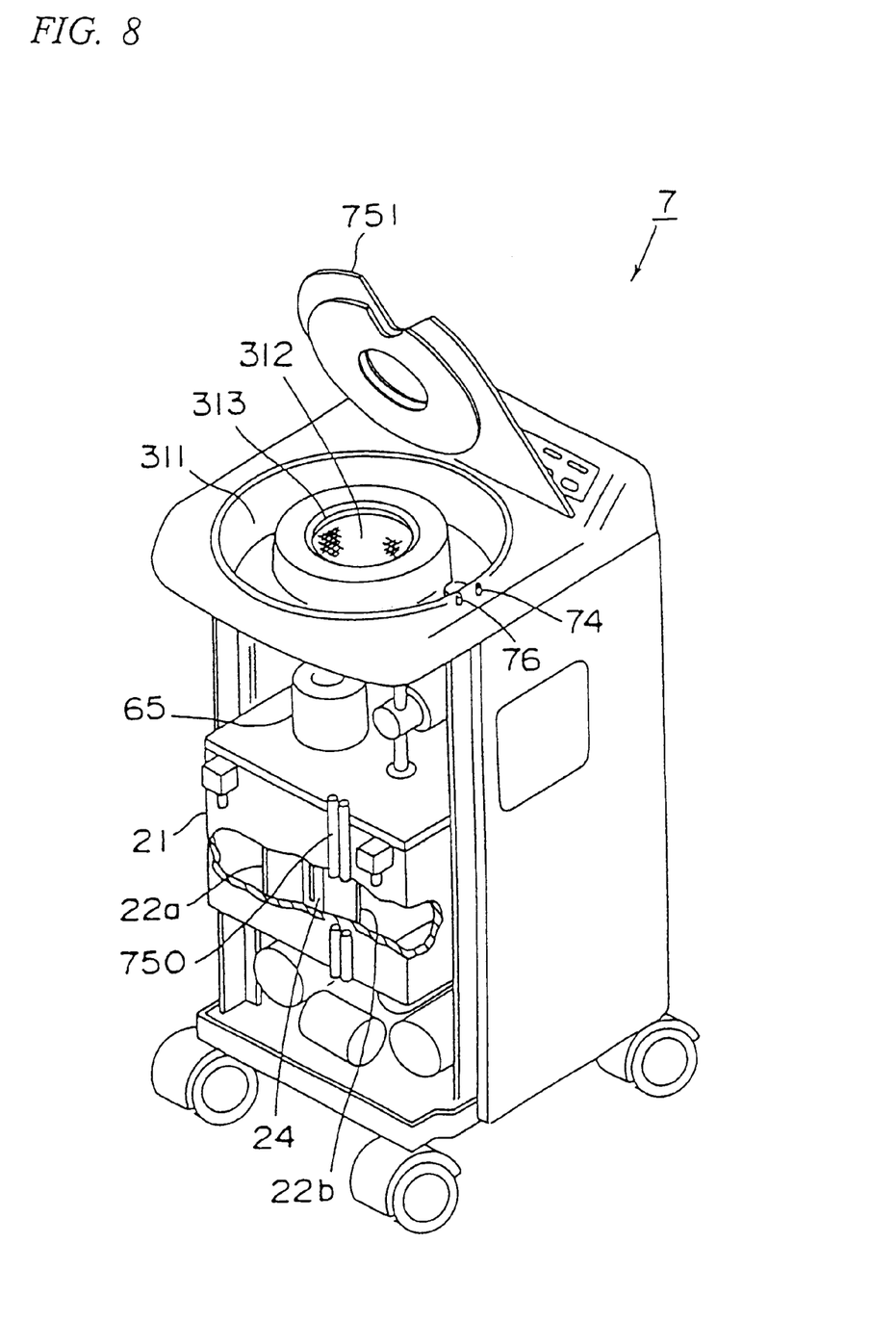
FIG. 8 is a perspective view indicating the outward appearance of the sterilizing apparatus of FIG. 6.

The outward appearance of the sterilizing apparatus 7 is as shown in FIG. 8. In FIG. 8, the same parts as in FIG. 6 are indicated by the same reference numerals. At the same time, in FIG. 8, a decorative plate at the front face of the apparatus is removed to show the electrolytic cell 21, etc. inside the apparatus. Moreover, the electrolytic cell 21 is displayed in partly cutaway in order to show the positive electrode 22a, negative electrode 22b and ion exchange film 24. A reference numeral 750 is a discharge pipe. When the discharge pipe 750 is inclined to the front face of the sterilizing apparatus 7 about a lower part of the electrolytic cell 21, the acidic electrolytic water 20a and alkalic electrolytic water 20b in the electrolytic cell 21 are mixed, neutralized and discharged outside the apparatus.

Figure 9:
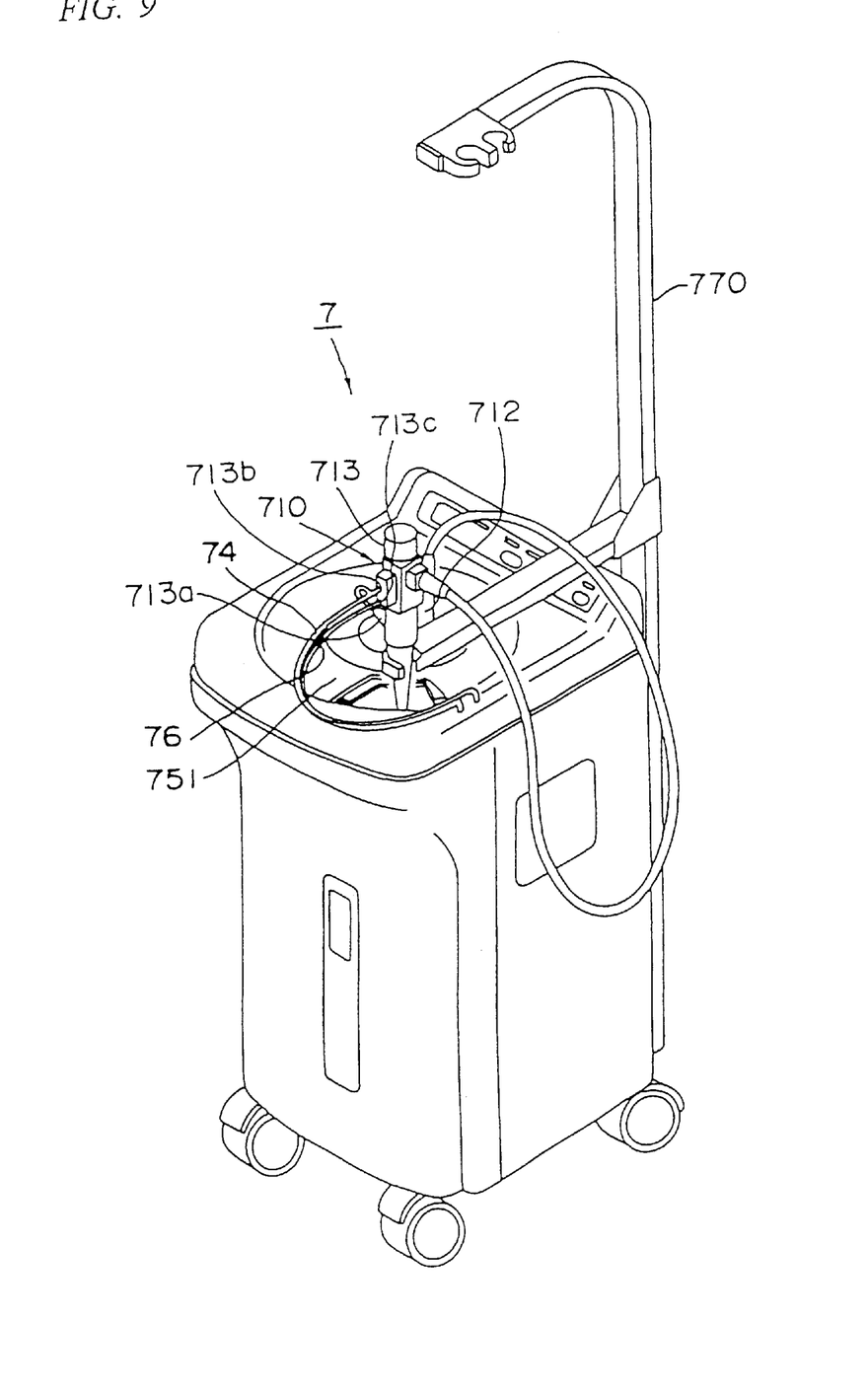
FIG. 9 is a perspective view of a state when an endoscope is sterilized by the sterilizing apparatus of FIG. 6.

FIG. 9 shows an arrangement how the sterilizing apparatus 7 and the endoscope 710 are positioned to sterilize the endoscope 710 with the sterilizing apparatus 7. In other words, FIG. 9 shows winding and accommodating the insertion part 711 in the sterilization bath 311 as discussed above. Lid 751 is then closed, and manipulation part 713 is held by a supporting tool 770 supported at the rear face of the sterilizing apparatus 7. Connection part 712 is held by the sterilization bath 312.

In each of the foregoing embodiments, the acidic electrolytic water 20a is adapted to freely drop from the sterilization bath 3 to the electrolyzation device 2 in order to make the sterilizing apparatus compact, cost-saving, and diminish failures, etc. through the reduction of the number of pumps. In other words, the sterilization bath 3 is located above the electrolytic cell 21. However, the positional relationship of the sterilization bath 3 and electrolytic cell 21 is not limited to this. For example, the sterilization bath 3 and the electrolyzation device 2 can be freely arranged if the acidic electrolytic water 20a is forcibly supplied from the sterilization bath 3 to the electrolytic cell 21.

The operation of the sterilizing apparatuses for medical instruments constructed as above will be depicted below. Since the operation related to the sterilization of medical instruments is basically the same in the sterilizing apparatuses 1, 5, 7, the operation of the sterilizing apparatus 7 of FIG. 8 will be discussed herein by way of example.

Approximately 10 l of plain water is poured into a bucket or similar like container, to which a prescribed amount of sodium chloride is added as described above, whereby a 0.05% sodium chloride aqueous solution is produced as electrolytic water 20. The electrolytic water 20 is injected into the accessory sterilization bath 312. The injected electrolytic water 20 is, through the return pipings 42a, 42b, distributed and injected to the acidic electrolytic water cell 21a and the alkalic electrolytic water cell 21b. As mentioned earlier, since the flow rate of the return pipings 42a and 42b is set to be 6:4, 6 l among the 10 l electrolytic water 20 is injected to the acidic electrolytic water cell 21a and 4 l is injected to the alkalic electrolytic water cell 21b.

Then, a power switch of the sterilizing apparatus 7 is actuated and a timer is set to start electrolyzing electrolytic water 20 one hour earlier than the time to start the sterilization. At the above-set time, the starting current of not larger than 5 A is provided from the power source 23 to the positive and negative electrodes 22a, 22b, so that the electrolytic water 20 is electrolyzed in the electrolytic cell 21. The sterilizing apparatus 7 is equipped with a weekly timer which can be set to start the electrolyzation at a constant time on week days.

The electrolyzation produces the acidic electrolytic water 20a in the acidic electrolytic water cell 21a which has the positive electrode 22a, and the alkalic electrolytic water 20b in the alkalic electrolytic water cell 21b with the negative electrode 22b. The electrolyzation is carried out for one hour so as to obtain the acidic electrolytic water 20a suitable for the sterilization. During this time, a lamp indicating that the electrolytic water is being prepared is turned on. It is generally said that microbes such as germs and the like do not survive in the environment of a PH of 2.7 or lower and an oxidation-reduction potential (ORP based on an Ag/AgCl electrode) of 100 mV or higher. Therefore, the acidic electrolytic water 20a suitable for the sterilization should have the PH of not higher than 2.7 and the oxidation-reduction potential of not lower than 1000 mV.

After of one hour, the sterilizing apparatus is ready for sterilization, and a lamp indicating completion of the preparation is turned on. The acidity and the oxidation-reduction potential of the acidic electrolytic water 20a deteriorate with time if the acidic electrolytic water 20a are left naturally, and are also deteriorated by the sterilization operation of medical instruments to be described later. As such, in order to maintain the acidic electrolytic water 20a at a specific value fit for the sterilization at all times, the keep current of about 1 A is fed to the positive and negative electrodes 22a and 22b in place of the starting current when the preparation is completed. It is confirmed with the use of a test paper that the acidic electrolytic water 20a holds the PH value and oxidation-reduction potential value in the above-mentioned predetermined range.

The preparation for starting the sterilization is completed in the above-described procedures. Now, the operation to sterilize the endoscope 710 will be depicted below. As described with reference to FIGS. 6 and 9, the endoscope 710 is set in the sterilizing apparatus 7. When a "sterilization switch" of the sterilizing apparatus 7 is manipulated, pumps 71, 73 are activated and the acidic electrolytic water 20a is supplied from the acidic electrolytic water cell 21a to the insertion part sterilization bath 311 of the sterilization bath 310. At the same time, pumps 75, 77 are driven to feed the acidic electrolytic water 20a from the acidic electrolytic water cell 21a into the manipulation part 713, insertion part 711 and connection part 712 of the endoscope 710. Accordingly, the interior of the manipulation part 713, insertion part 711 and connection part 712 is sterilized. Because of the nozzle 502 set at the feed pipings 70, 72 as described before, the acidic electrolytic water 20a is mixed with the gas and the mixture is sent to the sterilization bath 311. In the sterilization bath 311, the connection end part 500 generates the flow of the water in the opposite direction to the winding direction of the insertion part 711 as described above, so that the outer surface of the insertion part 711 can be sterilized effectively.

The acidic electrolytic water 20a overflowing from the sterilization bath 311 runs into the sterilization bath 312 and sterilizes the accessories. The acidic electrolytic water 20a flowing in the sterilization bath 312 is returned to the acidic electrolytic water cell 21a through the return piping 42a because the valve 43 is closed. When the acidic electrolytic water 20a returning to the acidic electrolytic water cell 21a passes through the filter 60 and coarse filter 67, solid substances, etc. removed from the endoscope 710 in the sterilization operation are filtered. The PH and oxidation-reduction potential of the acidic electrolytic water 20a returned to the electrolytic cell 21 are adjusted to be the above-described values by the action of the keep current. The acidic electrolytic water 20a. is again sent into the sterilization bath 311, manipulation part 713, insertion part 711 and connection part 712 by the pumps 71, 73, 75, 77.

In the above manner, the acidic electrolytic water 20a having constant PH and constant oxidation-reduction potential is circulated between the electrolytic cell 21 and sterilization bath 310, and between the sterilization bath 310 and interior of the endoscope, thereby sterilizing the endoscope 710. The sterilization in the sterilizing apparatus 7 takes 7 minutes per endoscope.

One endoscope 710 is completely sterilized in the above operation and is thereafter taken out from the sterilizing apparatus 7. Since the acidic electrolytic water 20a converts neutral water when left as it is, the acidic electrolytic water 20a remaining on the outer surface of the endoscope 710 and inside the manipulation part 713, insertion part 711 and connection part 712 eventually converts to the original neutral electrolytic water. Therefore, the conventional requirement to rinse the disinfectant is eliminated, and thus the sterilizing apparatus according to the present invention enables the sterilization of endoscopes in a short time.

According to the embodiments, while the acidic electrolytic water 20a is circulated, the PH and oxidation-reduction potential of the water 20a are adjusted and maintained at constant values, and more desirably, solid substances are removed from the water. Owing to this, approximately 20 endoscopes (corresponding to the number of inspections carried out in one day) can be repeatedly sterilized without exchange the acidic electrolytic water 20a.

After all inspections carried out in one day are finished, the discharge pipe 750 of the sterilizing apparatus 7 is inclined forward of the apparatus as shown in FIG. 8 to discharge the electrolytic water 20 in the electrolytic cell 21, for example, to a bucket or the like. Since the acidic electrolytic water 20a and the alkalic electrolytic water 20b in the electrolytic cell 21 are mixed when discharged from the discharge pipe 750, the electrolytic water 20 discharged to the container becomes neutralized water and therefore does not cause an environmental hazard even when let out to the drainage. The alkalic electrolytic water 20b is stored in the electrolytic cell 21 so as to bring about the above neutralization at the discharging time.

The acidic electrolytic water 20a maintained at the predetermined PH and oxidation-reduction potential values is circulated between the electrolytic cell 21 and sterilization bath 310 thereby to sterilize medical instruments. The time to start the next sterilization after one sterilization is finished is thus shortened. Regarding the sterilization of endoscopes, only parts of the endoscope in touch with the interior of the patients or humor are sterilized according to the embodiments, and therefore the endoscope can be easily set/removed to the sterilization bath 3.

Furthermore, to sterilize the endoscopes by circulating the acidic electrolytic water 20a reduces the consumption of the acidic electrolytic water, eliminates the necessity for exchanging the acidic electrolytic water, and eliminates water feed/discharge piping to the sterilizing apparatus.

In addition, since the electrolytic water is supplied/discharged by means of the bucket or the like in the embodiments, no positional limit is imposed on the sterilizing apparatus.

As is fully described hereinabove, according to the present invention, the acidic electrolytic water for sterilizing medical instruments stored in the sterilization bath is produced at the electrolytic cell, supplied to the sterilization bath and returned to the electrolytic cell from the sterilization bath. That is, the acidic electrolytic water is circulated between the electrolytic cell and the sterilization bath to sterilize the medical instruments. Accordingly, the time to start the next sterilization after the completion of one sterilization operation is shortened. Moreover, acidic electrolytic water is used as the sterilization liquid and the acidic electrolytic water remaining on the surface of medical instruments after the sterilization is neutralized with time. The sterilization liquid need not be rinsed away after sterilization, contrary to the conventional art, thereby achieving the sterilization of medical instruments in a short time. The sterilization is easily conducted simply by putting the medical instruments into the sterilization bath.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A sterilizing apparatus, comprising:

an electrolyzation device comprising an electrolytic cell, said electrolytic cell including an acidic electrolytic water cell and an alkalic electrolytic water cell, said electrolyzation device producing an acidic electrolytic water within said acidic electrolytic water cell and an alkalic electrolytic water within said alkalic electrolytic water cell by acting on an electrolytic water within both said acidic electrolytic water cell and alkalic electrolytic water cell, and applying a starting current to said electrolytic water within both said acidic electrolytic water cell and alkalic electrolytic water cell and thereafter applying a keep current smaller than the starting current to said acidic electrolytic water within said acidic electrolytic water cell and said alkalic electrolytic water within said alkalic electrolytic water cell;

a sterilization bath for receiving said acidic electrolytic water from said acidic electrolytic water cell; and a circulation device for circulating said acidic electrolytic water from said acidic electrolytic water cell to said sterilization bath, and back to said acidic electrolytic water cell.

2. The sterilizing apparatus according to claim 1, wherein said electrolyzation device performs the application of one of said starting current and said keep current based on a comparison of a characteristic of said electrolytic water with a threshold value for said characteristic.

3. The sterilizing apparatus according to claim 2, wherein said starting current is provided to said electrolytic water until said characteristic of said electrolytic water reaches said threshold value, and said keep current is thereafter provided to said electrolytic cell in order to maintain said characteristic at said threshold value.

4. The sterilizing apparatus according to claim 3, wherein said starting current is set so as to prevent said electrolytic water from being suddenly electrolyzed, thus restricting generation of free chlorine.

5. The sterilizing apparatus according to claim 3, wherein said starting current is not larger than 5 amperes.

6. The sterilizing apparatus according to claim 3, wherein said circulation device comprises return piping through which said acidic electrolytic water is returned from said sterilization bath to said acidic electrolytic water cell, said return piping including a filter for removing solid material in said acidic electrolytic water returning from said sterilization bath to said acidic electrolytic water cell.

7. The sterilizing apparatus according to claim 6, wherein said circulation device comprises feed piping connecting said acidic electrolytic water call with said sterilization bath, said feed piping having a connection end part for generating a flow of said acidic electrolytic water within said sterilization bath, said connection end part being arranged at a position where said feed piping is connected with said sterilization bath.

8. The sterilizing apparatus according to claim 7, wherein said feed piping includes an air feed inlet to aerate said acidic electrolytic water supplied to the sterilization bath.

9. The sterilizing apparatus according to claim 6, wherein said sterilization bath comprises an annular sterilization bath for storing an internal insertion part of an endoscope, and an accessory sterilization bath integrally formed with said annular sterilization bath and being located at a central part of said annular sterilization bath and to which said acidic electrolytic water overflowing from said annular sterilization bath runs in.

10. The sterilizing apparatus according to claim 9, wherein said circulation device comprises a first feed piping connected at a bottom part of said annular sterilization bath and through which said acidic electrolytic water is fed to said annular sterilization bath, and a second feed piping for feeding said acidic electrolytic water into said endoscope and being detachable to said endoscope.

11. The sterilizing apparatus according to claim 10, wherein said first feed piping has a connection end part at the bottom part for generating a flow of said acidic electrolytic water within said sterilization bath along with a shape of said annular sterilization bath.

12. The sterilizing apparatus according to claim 11, wherein said annular sterilization bath has a recessed part storing said connection end part at the bottom part of said annular sterilization bath.

13. The sterilizing apparatus according to claim 12, wherein said second feed piping is connected to a manipulation part of said endoscope, a part of said acidic electrolytic water fed to said manipulation part being drained to said annular sterilization bath through an inside of said internal insertion part, a remainder of said acidic electrolytic water fed to said manipulation part being fed to a connection part of said endoscope and drained to said accessory sterilization bath.

14. The sterilizing apparatus according to claim 13, wherein said first and second feed piping includes an air feed inlet to aerate said acidic electrolytic water supplied to said annular sterilization bath and endoscope.

15. A sterilizing method, comprising:

producing an acidic electrolytic water by performing electrolysis of an electrolytic water in an electrolytic cell and by applying a starting current to said electrolytic water and thereafter applying a keep current smaller than said starting current, said electrolytic cell including an acidic electrolytic water cell in which said acidic electrolytic water is produced and an alkalic electrolytic water cell; and circulating said acidic electrolytic water from said acidic electrolytic water cell to a sterilizing bath, and from said sterilizing bath to said acidic electrolytic water cell.

16. The sterilizing method according to claim 15, further comprising aerating said acidic electrolytic water circulated to said sterilizing bath.

\* \* \* \* \*